United States Patent [19]

Beadle et al.

[11] Patent Number: 5,690,950
[45] Date of Patent: Nov. 25, 1997

[54] INSECTICIDAL ALIPHATIC CARBOXYLIC ACID COMPOSITONS

[75] Inventors: James R. Beadle, San Diego, Calif.;
Lee R. Zehner, Brookeville, Md.;
Gilbert V. Levin, Annapolis, Md.;
James P. Saunders, Rockville, Md.;
Robert C. Bozsa, Silver Spring, Md.

[73] Assignee: Biospherics, Inc., Beltsville, Md.

[21] Appl. No.: 725,982

[22] Filed: Oct. 4, 1996

Related U.S. Application Data

[63] Continuation of Ser. No. 328,875, Oct. 25, 1994, abandoned.
[51] Int. Cl.$^6$ .......................... A01N 33/12; A01N 37/02; A01N 37/06; A01N 25/06; A01N 25/12
[52] U.S. Cl. .............................. 424/405; 514/919
[58] Field of Search ............... 424/405; 514/919, 514/557

[56] References Cited

U.S. PATENT DOCUMENTS

| | | | |
|---|---|---|---|
| 2,627,487 | 2/1953 | Drake et al. | 514/919 |
| 4,166,107 | 8/1979 | Miller et al. | 424/405 |
| 4,983,390 | 1/1991 | Levy | 424/404 |
| 5,182,096 | 1/1993 | Portas et al. | 424/405 |
| 5,399,344 | 3/1995 | Yang et al. | 424/84 |
| 5,407,656 | 4/1995 | Roozdar | 252/187.21 |
| 5,556,881 | 9/1996 | Grahn Marisi | 514/557 |

OTHER PUBLICATIONS

Dialog report including Sep. 3, 1993 Phoenix Gaxette article.

Press Advisory, U.S. Environmental Protection Agency, Sep. 16, 1994.

Reregistration Eligibility Document for Citric Acid, Case 4024, U.S. EPA, Jun. 1992.

Anonymous, "Citric Acid Finds Niche in Food Treatment," Chemical Marketing Reporter, Jun. 28, 1993.

James Giese, Anti–microbials: Assuring food safety, Food Technology, p. 102, Jun. 1994.

Anderson, M. E. and Marshall, R.T. "Reducing Microbial Populations.. Journal of Food Science", vol. 55, p. 903, 1990.

Doores,S. Organic Acids, in Antimicrobials in Food, Es. Davidson and Branen, Barcel Dekker, N.Y. 1993, pp. 95–135.

Anonymous, Food Acidulants have many functions.. Food Engineering, Mar. 1979, p. 156.

*Primary Examiner*—Thurman K. Page
*Assistant Examiner*—Murthy Sikha
*Attorney, Agent, or Firm*—William S. Ramsey

[57] ABSTRACT

A composition and method for killing insect larvae, in particular, fly larvae, in poultry houses, manure piles, or other sites of habitation are disclosed. The composition consists of one or more $C_2$ to $C_6$ aliphatic carboxylic acids or alkali metal, alkaline earth, ammonia, primary, secondary, tertiary, or quaternary ammonium salts in an acceptable formulation for larvacides. The formulation may be applied dry, as an aerosol, or in aqueous or organic solvents.

10 Claims, No Drawings

INSECTICIDAL ALIPHATIC CARBOXYLIC ACID COMPOSITONS

This application is a continuation of application Ser. No. 08/328,875, filed Oct. 25, 1994, now abandoned.

BACKGROUND OF THE INVENTION

1. Field of the Invention

This invention relates to methods and chemical compositions for the destruction of insect larvae.

2. Description of Related Art

Control of houseflies and other insects in commercial, industrial, and residential settings has become difficult because of the development of resistance to the traditional chemicals used. Existing methods of control of houseflies around livestock dwellings are based on synthetic chemicals, bait and light traps, and cultural techniques such as removal of animal manure and general sanitation. There is a strong need for new methods of control based on a different, safe for humans and animals, mode of action.

Citric acid and potassium sorbate, among other compounds, have been proposed by the Environmental Protection Agency for exemption from the pesticide regulations when these substances are sold, distributed, or used as pesticides. (Press Advisory, U.S. Environmental Protection Agency, Sep. 16, 1994).

Citric acid is registered with the Environmental Protection Agency as a disinfectant, sanitizer, fungicide, and scale remover. (Reregistration Eligibility Document for Citric Acid, Case 4024, U.S. Environmental Protection Agency, June 1992).

Citric acid, acetic acid, and lactic acid have been found to be effective as anti-microbial agents when used to treat animal carcasses and seafood. Coliform and aerobic microorganisms were reduced when citric acid was applied to beef carcasses. It was speculated that the reductions in bacterial counts were caused by the stress introduced into the environment by the acids. Bacterial growth was inhibited when the acids were applied immediately after carcass dehiding and pre-washing. (Anonymous, "Citric Acid Finds Niche in Food Treatment", *Chemical Marketing Reporter*, Jun. 28, 1993).

The effectiveness of carboxylic acids as anti-microbial agents is known to be a function of the pH of the food in which the agents are used. As food pH increased from 1 to 7, the concentration of the active anti-microbial form, the undissociated acid, decreased 2 orders of magnitude. For example, 0.6, 0.15, and 0.7% of sorbic, benzoic, and propionic acids respectively exist as the undissociated form at pH 7. Consequently, these acids are not effective antimicrobials at this pH. (James Giese, "Anti-microbials: Assuring Food Safety", *Food Technology*, p. 102, June 1994). Most bacteria in food grow best at a neutral pH (6.7 to 7.5). The organic acids act as anti-microbials by lowering pH and thus retarding bacterial growth (Anderson, M. E. and Marshall, R. T. "Reducing Microbial Populations of Beef Tissues: Concentration and Temperature of an Acid Mixture", *Journal of Food Science*, vol. 55, p. 903, 1990; and Doores, S., "Organic Acids", in *Antimicrobials in Food*, Eds. Davidson, P. M. and Branen, A. L., (Marcel Dekker, Inc., N.Y 1993), pp. 95–135.)

The use of the carboxylic acids and salts of this invention as insecticides has not been previously disclosed.

In contrast to the situation in foods, typical fly larvae environments, for example chicken manure, have alkaline pH values between 7 and 9. These values are too high to permit the organic acids to function as anti-microbials. In addition, the salts of the organic acids are effective as larvacides. This suggests the observed larvacidal activity and the pH-derived anti-microbial activity of these compounds are not related in any obvious way.

The organic acids of this invention have been proven safe for humans and domestic animals at larvacidal levels, and, in fact, are generally recognized as safe as food additives. These insecticides are completely biodegraded to $CO_2$ and water and therefore are environmentally benign. The larvacides of this invention interfere with the insect life cycle at the larval stage, thus interrupting the life cycle prior to the insect's emergence as a pest. These larvacides are stable when stored dry or in solution and are economical when used as recommended.

SUMMARY OF THE INVENTION

This invention provides a method and formulations for preventing insect infestations, especially infestation by houseflies. The insects are killed at the larval stage by means of application of specified organic carboxylic acids, especially citric acid and citrate salts, to the manure of domesticated animals, to fixed and mobile storage containers, and to garbage and refuse dumps or to any accidental or organic material storage site where insect larvae may be harbored.

The active compounds are $C_2$ to $C_6$ aliphatic carboxylic acids and their salts, excluding acetic acid and the salts of acetic acid.

The active compounds may be formulated with conventional insecticide adjuvants and vehicles and may be applied as dry powders, as granules, as aerosols, aqueous solutions, or solutions in organic solvents.

DESCRIPTION OF THE PREFERRED EMBODIMENTS

This invention is a method and formulations for control of insects which have a site of habitation in food storage sites, manure, garbage, trash, soil, or sanitary landfills. The term "insect" includes a member of the class Insecta as well as spiders, mites, ticks, centipedes, and similar members of the phylum Arthropoda. Insects are susceptible to destruction by treatment with organic carboxylic acids while at the larval stage of development. Insects of the order Diptera are most susceptible. The most preferred target insects are those of the family Muscidae, which include the housefly, face fly, and stable fly, among others.

Sites of habitation which may be treated with the larvacide include food and agricultural product storage sites, domesticated animal barns, poultry farm buildings, garbage and trash dumps, fixed and mobile storage containers for garbage or refuse in homes and industry, sanitary landfills, or any other sites, including accidental sites, where insect larvae may be harbored.

The claimed compounds are $C_2$ to $C_6$ saturated and unsaturated aliphatic carboxylic acids that contain between 1 and 4 carboxylic acid (—COOH) groups, 0 to 5 hydroxyl (alcohol) groups, 0 to 3 carbonyl (=C=O) groups, 0 to 2 carbon-carbon double bonds, and 0 to 1 carbon-carbon triple bonds and their salts excluding acetic acid and salts of acetic acid. Salts include but are not limited to $Na^+$, $K^+$, $Ca^{++}$, $Li^+$, $Mg^{++}$, $NH_4^+$, primary, secondary, tertiary, or quaternary ammonium, salts of the compounds. The term "compound" in this disclosure means the above carboxylic acids and their salts. The compounds include common organic acids such as citric acid, lactic acid, propionic acid, maleic acid, tartaric acid, gluconic acid, fumaric acid, adipic acid, sorbic acid, malonic acid, malic acid, and their salts. All stereoisomers of the above carboxylic acids and salts having chiral centers are active as larvacides, as are those carboxylic acids and salts cited above which do not have optically active centers. Mixtures of two or more of the carboxylic acids may be used; likewise mixtures of acids and their respective salts, or mixtures of one or more acids and one or more salts may be used.

Salts of acetic acid are not effective as larvacides.

Formic acid and salts of formic acid probably are effective larvacides but are not suitable for this use because of the animal toxicity of these compounds.

The exact mode of action of the above compounds is unknown. Without wishing to be bound by this discussion of the mode of action, we believe activity may be attributed to one or more of the following factors: 1. A decrease in the pH of the material adjacent to the larvae, which causes a deleterious effect on the larvae, 2. An increase in the osmotic potential in the material adjacent to the larvae, causing dehydration, 3. The disruption of the citric acid cycle within the larvae, perhaps with some other unknown mechanism. It is possible that, in addition to controlling the larval stage, the compounds may effect some control over the adult stage insects.

The compounds preferentially are applied to the treated environments at a rate of 1 to 100 grams of active compound per square foot of treatment area. This range of application rates is approximately equivalent to 0.4% to 40% by weight of active compound to manure. Typically applications are made one to three times per week. In certain circumstances applications may be made as infrequently as once a month or as frequently as 12 times per day. The active compounds and formulations should be applied in the absence of high wind and should not be sprayed directly onto animals which might inhale the spray.

The compounds may be formulated with adjuvants and vehicles such as water or organic solvents as are other insecticides. Dyes, such as methylene blue, may be included in the formulation at concentrations from 0.1 to 2.0% by weight of active compound in order to aid in the even application of the larvacide formulation. Surfactants, such as sodium lauryl sulfate, may be included at concentrations from 0.1 to 5.0% by weight of compound to aid in the penetration or distribution of liquid formulations. Liquid formulations may be made in various vehicles, such as water or organic solvents. A drift reducing agent, such as carboxymethylcellulose or starch, may be included at concentrations from 0.1 to 5.0% by weight of active compound in order to aid in the application of liquid larvacide formulations by reduction of misting. Buffering agents, such as sodium or potassium salts of phosphoric acid, may be included at concentrations from 0.1 to 50% by weight of compound to provide a desirable pH for the formulation. Fragrances, such as peppermint oil, may be included at concentrations from 0.1 to 2.0% by weight compound to counter the odor of sites of habitation to be treated.

A preferred larvacide formulation may be prepared as follows:

| Ingredient | Grams |
| --- | --- |
| Sodium propionate | 400 |
| Methylene blue | 4 |
| Sodium lauryl sulfate | 4 |
| Peppermint oil | 6 |
| Water | 600 |

Such a formulation is applied by spraying or as an aerosol.

The claimed active compounds and formulations of them may be applied dry or as aqueous solutions or as organic solvent solutions. Suitable organic solvents include methanol, ethanol, and dimethylsulfoxide. Solutions may be sprayed using hand-held or back-pack sprayers. Alternatively, solutions may be sprayed using a fixed, automatically-timed spray system. Solids may be applied by dusting, by spreading as granules, or as an aerosol.

EXAMPLE 1

Citric Acid and Sodium Citrate Control of Houseflies

Aqueous solutions of citric acid and sodium citrate were each applied to a souffle cup containing 100 grams of fresh poultry manure at the rate of 0, 4, and 8% w/w (active compound/manure). Each cup was seeded with 25 one-day old housefly larvae. After 10 days pupae were extracted and counted.

| Treatment* | Percent Control |
| --- | --- |
| Check | 10 |
| Citric Acid (4% w/w) | 100 |
| Citric Acid (8% w/w) | 100 |
| Sodium Citrate (4% w/w) | 62 |
| Sodium Citrate (8% w/w) | 100 |

*Rates of active compounds (applied as 40% aqueous solution) calculated as percentage of manure weight.

This showed that citric acid and sodium citrate were active in preventing the pupation, and thereby preventing the maturation, of housefly larvae.

EXAMPLE 2

Citric Acid and Control of Houseflies in a Chicken Pen 1

Ten white leghorn chickens were housed in cages contained within each of two side-by-side, 7×2.3 meter, screened pens. Chicken manure was allowed to accumulate under the cages on a concrete floor for several days, after which time the pens were completely cleaned out and the experiment started. Starting two days after the pens were cleaned out, citric acid (40% w/w aqueous solution) was applied directly to the newly accumulated chicken manure on the concrete floor under one pen. The citric acid was applied using a hand sprayer at the rate of 8% w/w citric acid to freshly accumulated manure or about 18 grams citric acid per square foot of manure surface. Applications were continued every other day for 14 days for a total of 8 applications. The check pen received equivalent applications of water.

On the tenth day, approximately 2000 adult houseflies (Musca domestica) were released into each pen. Fly numbers in each pen were determined by trapping with a Tiger Farm Box Trap starting 1 week after the last application. After 6 weeks of trapping, total flies caught were 75 times higher in the check pen than in the treated pen effecting a control rate of 98.7 percent.

| Days After Last Treatment | Number of Adult Houseflies Caught | |
|---|---|---|
| | Treated* | Untreated |
| 39 | 12 | 182 |
| 48 | 0 | 6229 |
| 53 | 114 | 3046 |
| Total | 126 | 9457 |

*Application of citric acid at 8% w/w citric acid to fresh manure as a 40% w/w aqueous solution made every other day for 14 days.

This showed that treatment of chicken manure with citric acid followed by exposure to houseflies greatly inhibited the subsequent infestation of the manure by houseflies.

EXAMPLE 3

Citric Acid and Control of Houseflies in a Chicken Pen 2

Twenty white leghorn chickens were housed in cages contained within each of two side-by-side, 7×2.3 meter, screened pens. Chicken manure was allowed to accumulate under the cages on a concrete floor for several days, after which time the floors of the pens were completely cleaned. Starting two days after the pens were cleaned, citric acid (40% w/w aqueous solution) was applied to the freshly accumulating manure in one pen with a hand sprayer at the rate of 8% w/w of the freshly accumulated manure, or 18 grams per square foot of manure surface. Applications were continued every other day for 20 days, for a total of 11 applications. The check pen received equal applications of water only.

On the twelfth day, approximately 2000 adult houseflies (*Musca domestica*) were released into each pen. Fly numbers in each pen were determined by trapping with a Tiger Farm Box Trap. After 3 weeks of trapping, total flies caught were 22 times higher in the check pen than in the treated pen.

| Days After Last Treatment | Number of Adult Houseflies Caught | |
|---|---|---|
| | Treated* | Untreated |
| 13 | 294 | 7308 |
| 20 | 513 | 1019 |
| 27 | 450 | 10698 |
| Total | 1257 | 28197 |

*Application of citric acid at 8% w/w citric acid to fresh manure as a 40%, w/w aqueous solution made every other day for 20 days.

This showed that treatment of chicken manure with citric acid followed by exposure to houseflies greatly inhibited the subsequent infestation of the manure by houseflies.

EXAMPLE 4

Compounds and Prevention of Housefly Pupation

Aqueous solutions of citric acid, lactic acid, gluconic acid, sodium adipate, calcium propionate, and sodium acetate were each applied to respective containers holding 384 grams of fresh poultry manure at the rate of 4% w/w (anion of compound/manure). Each container was seeded with 25 one day old housefly larvae. After ten days pupae were extracted and counted.

| Treatment | Percent Control* |
|---|---|
| Citric Acid | 85 |
| Lactic Acid | 85 |
| Gluconic Acid | 100 |
| Sodium Adipate | 100 |
| Calcium propionate | 55 |
| Sodium Acetate | 0 |

*Calculated using Abbott's Formula for check having 400 grams manure and no added compound.

This shows the activity of citric acid, lactic acid, gluconic acid, sodium adipate, calcium propionate, in preventing housefly pupation. Sodium acetate was inactive in preventing housefly pupation.

It will be apparent to those skilled in the art that the examples and embodiments described herein are by way of illustration and not of limitation, and that other examples may be used without departing from the spirit and scope of the present invention, as set forth in the appended claims.

We claim:

1. A method for killing insect larvae comprising the step:
   applying a larvacidal amount of one or more $C_2$ to $C_6$ aliphatic carboxylic acids excluding acetic acid to the site of habitation of said insect larvae.

2. The method of claim 1 wherein the insect is a member of the class Insecta.

3. The method of claim 1 wherein the insect is a member of the order Diptera.

4. The method of claim 1 wherein the insect is a member of the family Muscidae.

5. The method of claim 1 wherein the insect is a housefly, face fly, or stable fly.

6. The method of claim 1 wherein the insect is a housefly.

7. The method of claim 1 wherein the $C_2$ to $C_6$ aliphatic carboxylic acid is citric acid, lactic acid, propionic acid, maleic acid, tartaric acid, gluconic acid, fumaric acid, adipic acid, sorbic acid, malonic acid, or malic acid.

8. The method of claim 1 wherein the $C_2$ to $C_6$ aliphatic carboxylic acid is citric acid.

9. The method of claim 1 wherein the amount of one or more $C_2$ to $C_6$ aliphatic carboxylic acids excluding acetic acid applied is from 0.4% to 40% by weight to weight of site of habitation material.

10. The method of claim 1 wherein the one or more $C_2$ to $C_6$ aliphatic carboxylic acids excluding acetic acid are applied dry as a dust, granule, or aerosol, as an aqueous solution, or as a solution in organic solvents.

* * * * *